United States Patent
Gao (10) Patent No.: US 10,761,418 B2
(45) Date of Patent: Sep. 1, 2020

(54) IMAGING METHOD AND IMAGING SYSTEM

(71) Applicant: Beijing Neusoft Medical Equipment Co., Ltd., Beijing (CN)

(72) Inventor: Shang Gao, Beijing (CN)

(73) Assignee: Beijing Neusoft Medical Equipment Co., Ltd., Beijing (CN)

(*) Notice: Subject to any disclaimer, the term of this patent is extended or adjusted under 35 U.S.C. 154(b) by 165 days.

(21) Appl. No.: 15/942,578

(22) Filed: Apr. 2, 2018

(65) Prior Publication Data

US 2018/0284594 A1    Oct. 4, 2018

(30) Foreign Application Priority Data

Mar. 31, 2017   (CN) .......................... 2017 1 0210855

(51) Int. Cl.
*G03B 42/02*    (2006.01)
*A61B 6/00*    (2006.01)
(Continued)

(52) U.S. Cl.
CPC .......... *G03B 42/025* (2013.01); *A61B 6/0457* (2013.01); *A61B 6/4452* (2013.01);
(Continued)

(58) Field of Classification Search
CPC ......... A61B 6/457; A61B 6/4021; A61B 6/52; A61B 6/0457; G03B 42/025
See application file for complete search history.

(56) References Cited

U.S. PATENT DOCUMENTS

2012/0002782 A1    1/2012  Yoshida et al.
2012/0155609 A1*   6/2012  Lemminger ........... A61B 6/032
                                                    378/62
2013/0077745 A1*   3/2013  Wang ....................... A61B 6/52
                                                    378/62

FOREIGN PATENT DOCUMENTS

CN    101262820 A    9/2008
CN    102068294 A    5/2011
(Continued)

OTHER PUBLICATIONS

Moore et al, "The Centroid in 2D via the First Moment Integral", Mechanics Map, published Jan. 23, 2016; Retrieved from internet [Nov. 29, 2019], Retrieved from url <adaptivemap.ma.psu.edu/websites/A2_moment_intergrals/centroids_2d/centroids2d.html>. (Year: 2016).*

(Continued)

*Primary Examiner* — Yara B Green
(74) *Attorney, Agent, or Firm* — Kilpatrick Townsend & Stockton, LLP (57) ABSTRACT

An imaging method is provided. In an example, the imaging method includes a first X-ray image including a ROI of a subject is taken by an image capturing device, a position of the ROI in the first X-ray image is determined, a moving distance and a moving direction for a positioning system is determined based on the position of the ROI in the first X-ray image, and the positioning system is capable of being moved to adjust a positional relationship between the image capturing device and the subject, the positioning system is moved based on the moving distance and the moving direction, and a second X-ray image including the ROI is taken by the image capturing device, and the ROI is located in a center position of the second X-ray image.

14 Claims, 5 Drawing Sheets

(51) Int. Cl.
    *A61B 6/04* (2006.01)
    *G06T 7/60* (2017.01)
(52) U.S. Cl.
    CPC .............. *A61B 6/545* (2013.01); *A61B 6/588* (2013.01); *A61B 6/589* (2013.01); *G06T 7/60* (2013.01)

(56) References Cited

FOREIGN PATENT DOCUMENTS

| | | | |
|---|---|---|---|
| CN | 102961154 | A | 3/2013 |
| CN | 103181775 | A | 7/2013 |
| CN | 104203104 | A | 12/2014 |
| CN | 104352246 | A | 2/2015 |
| CN | 104414677 | A | 3/2015 |
| CN | 105147311 | A | 12/2015 |
| CN | 106344053 | A | 1/2017 |
| CN | 106388851 | A | 2/2017 |

OTHER PUBLICATIONS

State Intellectual Property Office of the People's Republic of China, Office Action and Search Report Issued in Application No. 201710210855.0, dated Sep. 2, 2019, 26 pages(Submitted with Machine Translation).

State Intellectual Property Office of the People's Republic of China, Office Action and Search Report Issued in Application No. 2017102108550, dated May 18, 2020, 40 pages, (Submitted with Machine Translation).

* cited by examiner

IMAGING METHOD AND IMAGING SYSTEM

CROSS REFERENCE TO RELATED APPLICATIONS

This application claims priority to Chinese Patent Application No. 201710210855.0 entitled "Imaging Method and Imaging System" filed on Mar. 31, 2017, the entire content of which is incorporated herein by reference.

TECHNICAL FIELD

The present disclosure relates to an imaging method of a medical imaging device and an imaging system.

BACKGROUND

An angiography machine is a medical imaging device that supports a doctor to perform examination or surgery. The angiography machine may display an image of internal tissues of a subject dynamically through X-rays. When an image is taken for a subject by using the angiography machine, a region of interest of the subject should be placed within a scanning field of view, for example, a center of the field of view. Therefore, when the subject lies on a scanning bed, it is desired to perform X-ray scanning while moving a positioning system until the region of interest is moved to the center of the field of view. Then, the subject can be examined. The positioning system may include a scanning bed and a gantry. Moving the positioning system may include moving the scanning bed (to be referred to as the bed hereinafter), or the gantry or both of them.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The accompanying drawings herein, which are incorporated in the description and constitute part of the description, illustrate examples consistent with the present disclosure and serve to explain the principle of the present disclosure together with the description.

DETAILED DESCRIPTION

Figure 1:
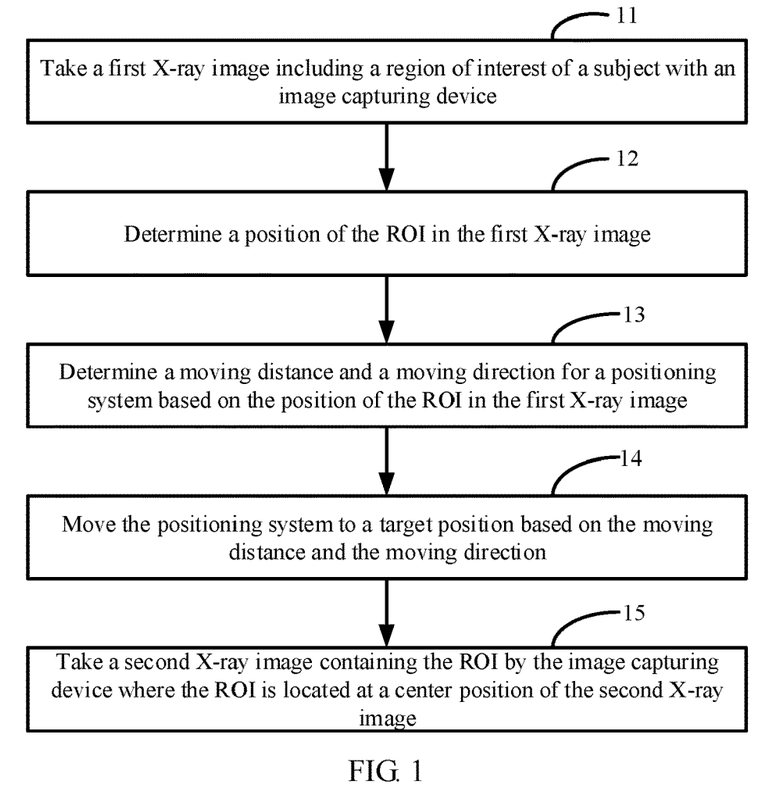
FIG. 1 is a flowchart illustrating an imaging method according to an example of the present disclosure.

FIG. 1 is a flowchart illustrating an imaging method according to an example of the present disclosure. The imaging method may be used to perform imaging for internal tissues of a subject through X-rays, for example, perform subtraction imaging for blood vessels of the subject. The process of the imaging method may include blocks 11-15.

At block 11, a first X-ray image including a region of interest of a subject may be taken with an image capturing device.

In an example of the present disclosure, when x-rays penetrates through a detected part of a subject, the first X-ray image including an image of the detected part is generated based on detected X-rays. A region indicating the detected part in the first X-ray image may be regarded as a region of interest (ROI), such as regions indicating blood vessel, heart, coronary artery and coronary vein in an angiography image. If the ROI is not contained in the first X-ray image, it indicates that the detected part does not appear within an X-ray radiation range. At this time, a positioning system may be moved until that the detected part appears within the X-ray radiation range, where the ROI may be located in any position of the first X-ray image.

At block 12, a position of the ROI in the first X-ray image is determined.

In an example of the present disclosure, the position of the ROI in the first X-ray image may be determined by determining a distance and a positional direction between a center point of the first X-ray image and a center point of the ROI in the first X-ray image. The distance and the positional direction between a center point of the first X-ray image and a center point of the ROI in the first X-ray image may be taken as a center point positional relationship. In other words, the position of the ROI in the first X-ray image may be represented by the center point positional relationship.

Figure 2:
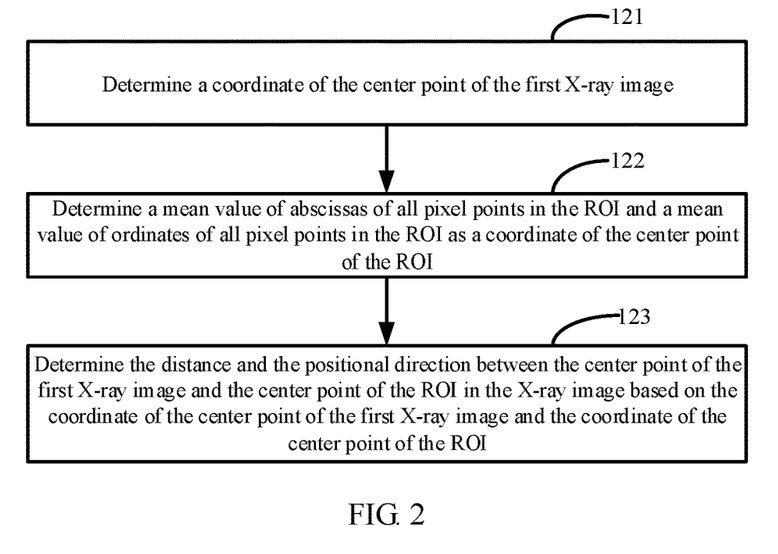
FIG. 2 is a flowchart illustrating a method of determining a position of a region of interest in a first X-ray image according to an example of the present disclosure.

FIG. 2 is a flowchart illustrating a method of determining a position of a ROI in a first X-ray image according to an example of the present disclosure. As shown in FIG. 2, block 12 may include sub-blocks 121-123.

At sub-block 121, a coordinate of the center point of the first X-ray image is determined.

In an example of the present disclosure, any pixel point in the first X-ray image is set as a zero coordinate. The coordinate of the center point of the first X-ray image may be determined based on a positional relationship between the pixel point which is set as the zero coordinate and the center point of the first X-ray image. For convenience of calculation, it is assumed that the coordinate of the center point of the first X-ray image is the zero coordinate, for example, the coordinate of the center point of the first X-ray image is (0, 0).

At sub-block 122, a mean value of abscissas of all pixel points in the ROI and a mean value of ordinates of all pixel points in the ROI are determined as a coordinate of the center point of the ROI.

Figure 3:
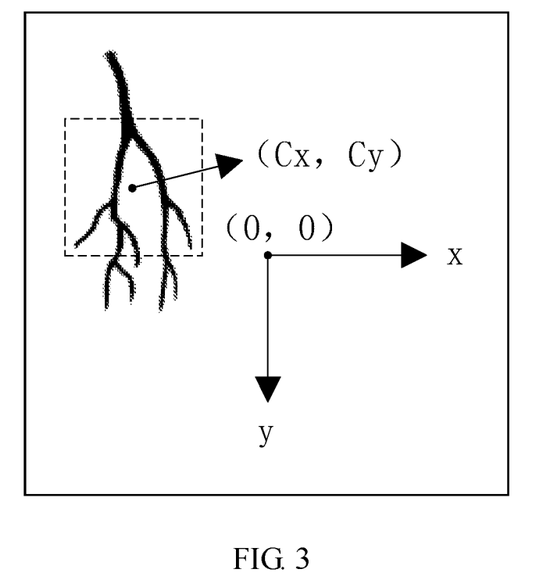
FIG. 3 is a schematic diagram illustrating a first X-ray image according to an example of the present disclosure.

FIG. 3 is a schematic diagram illustrating a first X-ray image according to an example of the present disclosure. In combination with FIG. 3, in the first X-ray image, a point with the coordinate as (0, 0) is the center point of the first X-ray image. A region inside the dotted line box shown in FIG. 3 indicates the ROI. It is assumed that the coordinate of the center point of the ROI is (Cx, Cy). The mean value of abscissas of all pixel points in the ROI is $$\frac{\sum_{P \in ROI} Px}{N},$$

and the mean value of ordinates of all pixel points in the ROI is $$\frac{\sum_{P \in ROI} Py}{N},$$

the coordinate of the center point of the ROI is $$(Cx, Cy) = \left( \frac{\sum_{P \in ROI} Px}{N}, \frac{\sum_{P \in ROI} Py}{N} \right).$$

Where P is any pixel point in the ROI, and the coordinate of the pixel point P is (Px, Py) and N indicates a number of pixel points in the ROI.

At sub-block 123, the distance and the positional direction between the center point of the first X-ray image and the center point of the ROI in the X-ray image may be determined based on the coordinate of the center point of the first X-ray image and the coordinate of the center point of the ROI.

In an example, the distance in the center point positional relationship is represented by a pixel distance. The pixel distance indicates a number of pixel points between the two center points. FIG. 3 is a schematic diagram illustrating a first X-ray image according to an example of the present disclosure. As shown in FIG. 3, it is assumed that the coordinate of the center point of the first X-ray image is (0, 0) and the coordinate of the center point of the ROI is $$(Cx, Cy) = \left( \frac{\sum_{P \in ROI} Px}{N}, \frac{\sum_{P \in ROI} Py}{N} \right),$$

the pixel distance between the center point of the first X-ray image and the center point of the ROI is:

$$\sqrt{Cx^2 + Cy^2} = \sqrt{\left(\frac{\sum_{P \in ROI} Px}{N}\right)^2 + \left(\frac{\sum_{P \in ROI} Py}{N}\right)^2}.$$

As shown in FIG. 3, the positional direction between the center point of the first X-ray image and the center point of the ROI is $$\tan^{-1} \frac{Cx}{Cy} \left( \text{i.e., } \tan^{-1} \frac{\sum_{P \in ROI} Px}{\sum_{P \in ROI} Py} \right)$$

degree deflecting from negative Y axis to negative X axis.

In another example, the distance in the center point positional relationship may also be represented by a physical distance between the two center points, for example, units of measurement for X axis and Y axis in the first X-ray image are both physical units, such as millimeter. Calculation method for calculating the physical distance between the center point of the first X-ray image and the center point of the ROI is the same as the calculation method in which the units of measurement for the X axis and Y axis being pixel units, and further detail is omitted for brevity.

Please refer to FIG. 1, at block 13, a moving distance and a moving direction for a positioning system may be determined based on the position of the ROI in the first X-ray image, where the positioning system is capable of being moved to adjust a positional relationship between the image capturing device and the subject.

Figure 4:
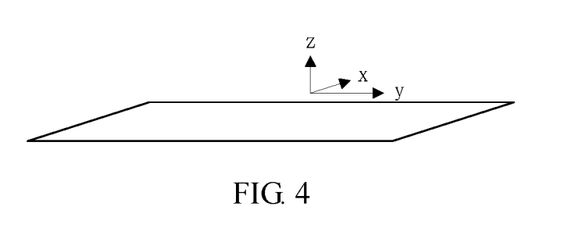
FIG. 4 is a schematic diagram illustrating a bed according to an example of the present disclosure.

In an example of the present disclosure, the positioning system may include a bed, or include a gantry, or include both of the bed and the gantry. In other words, when the positioning system is moved, the bed is moved, or the gantry is moved or both of the bed and the gantry are moved at the same time (there is relative movement between the bed and the gantry). In an example, a moving distance for at least one of the bed and the gantry may be determined based on the distance in the center point positional relationship, and a moving direction for at least one of the bed and the gantry may be determined based on the positional direction between the two center points. Take a case that the bed is moved as an example. Based on display of the first X-ray image relative to the position of the bed, x and y directions in the first X-ray image may be mapped to moving directions of the bed. As shown in FIG. 3 and FIG. 4, it is assumed that x, y directions along which the bed moves are consistent with the x, y directions in the first X-ray image.

Figure 5:
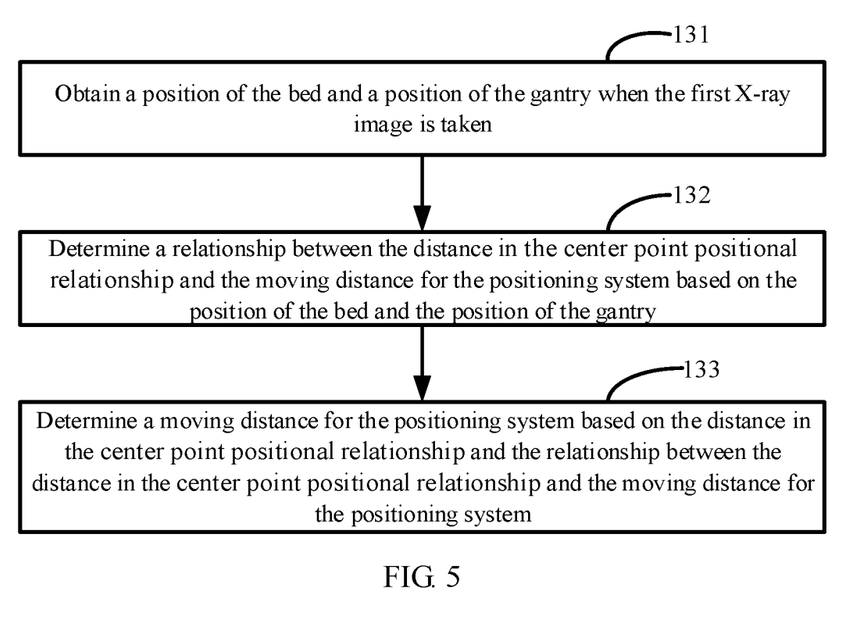
FIG. 5 is a flowchart illustrating a method of determining a moving distance and a moving direction for a positioning system according to an example of the present disclosure.

FIG. 5 is a flowchart illustrating a method of determining a moving distance and a moving direction for a positioning system according to an example of the present disclosure. As shown in FIG. 5, block 13 may include sub-blocks 131-133.

At sub-block 131, a position of the bed and a position of the gantry when the first X-ray image is taken are obtained.

In an example, the position of the bed is represented by a coordinate of any point on the bed (such as a coordinate of a center point of the bed), and the position of the gantry is represented by a coordinate of a middle point of a line connecting a transmitter and a receiver respectively mounted on opposite ends of the gantry. The receiver is opposite to the transmitter.

At sub-block 132, a relationship between the distance in the center point positional relationship and the moving distance for the positioning system may be determined based on the position of the bed and the position of the gantry.

The distance in the center point positional relationship and the moving distance for the positioning system may be in a proportional relationship. In an example, the distance in the center point positional relationship is represented by the pixel distance, and the relationship between the distance in the center point positional relationship and the moving distance for the positioning system is obtained by determining a unit moving distance corresponding to a unit pixel size in the first X-ray image.

Figure 6:
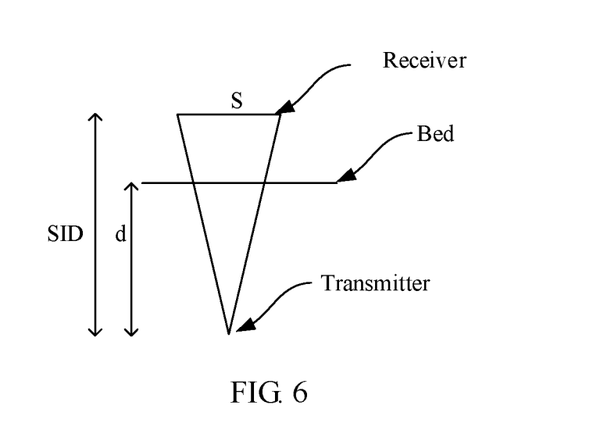
FIG. 6 is a schematic diagram illustrating a positional relationship between a bed, a transmitter and a receiver according to an example of the present disclosure.

In an example, the two opposite ends of the gantry are provided respectively with the transmitter and the receiver including a receiving units. The receiver is opposite to the transmitter. The pixel size of the first X-ray image is not only related to geometrical positions of the transmitter, the receiver and the bed, but also related to the size of each of the receiving units included in the receiver. FIG. 6 is a schematic diagram illustrating a positional relationship between a bed, a transmitter and a receiver according to an example of the present disclosure. Referring to FIG. 6, it is assumed that the size of each of the receiving units of the receiver is S mm, a distance from a focal point of the transmitter to the receiver is SID and a distance from the focal point of the transmitter to a surface of the bed is d, then the unit pixel size IS of the first X-ray image may be calculated based on the following formula (1):

$$IS = \frac{d}{SID} \cdot S \quad \text{formula (1)}$$

That is, when the first X-ray image is moved one pixel, the bed may need to move a distance of IS mm.

Please refer to FIG. 5, in sub-block 133, a moving distance for the positioning system may be determined based on the distance in the center point positional relationship and the relationship between the distance in the center point positional relationship and the moving distance for the positioning system.

One pixel point corresponds to one unit pixel size and a pixel distance may indicate a number of the pixel points. Therefore, it is known that the pixel distance may also indicate a number of the unit pixel size. It is assumed that the center position of the bed is (0, 0), then a central target position of the bed is (−Cx*IS, −Cy*IS) with unit of measurement being mm. The bed is moved a distance −Cx*IS along x direction and a distance −Cy*IS along y direction, where minus sign represents a negative axis direction.

In an example of the present disclosure, the moving distance for the bed may be determined based on the pixel distance between the center point of the first X-ray image and the center point of the ROI on the first X-ray image, and the unit moving distance.

In another example, the gantry is moved and the calculation method is similar to above. When the first X-ray image is moved one pixel, the gantry may need to move IS mm and the moving direction in the case that the gantry is moved is opposite to the moving direction in the case that the bed is moved. For example, assuming the x, y directions along which the bed is moved are the same with the x, y directions of the first X-ray image, the x, y directions along which the gantry is moved are opposite to the x, y directions of the first X-ray image.

In another example, both of the bed and the gantry are moved at the same time. At this time, there is relative movement between the bed and the gantry. Similar to the calculation method as above, when the first X-ray image is moved one pixel, the bed and the gantry may need to move IS mm in total.

Referring to FIG. 1, at block 14, the positioning system is moved to a target position based on the moving distance and the moving direction.

In an example of the present disclosure, after the moving distance and the moving direction for the positioning system are determined, the positioning system is controlled to move to the target position based on the moving distance and the moving direction. When the positioning system is at the target position, the detected part of the subject is located at a center position of the X-ray radiation range. In other words, when a second X-ray image is taken, the ROI in the second X-ray image is located at the center position of the second X-ray image.

At block 15, a second X-ray image including the ROI is taken by the image capturing device where the ROI is located at a center position of the second X-ray image.

The center point of the ROI may overlap the center point of the second X-ray image. In an example, the second X-ray images is taken. The second X-ray images may include at least one mask image which is taken in the case of no contrast medium being injected into blood vessels of the subject. The second X-ray images may also include at least one live image which is taken in the case of contrast medium being injected into the blood vessels of the subject. The mask image and the live image may be used to perform subtraction processing so as to obtain an enhanced image of the blood vessels. In other examples, the second X-ray images may be taken according to actual applications. In each of the second X-ray images, the ROI may be located in the center position of the second X-ray image.

In the present disclosure, the moving distance for the positioning system when the ROI in the first X-ray image is moved to the center position of the first X-ray image may be calculated based on the first X-ray image including the ROI which is taken previously. Then, the positioning system is controlled to move to the target position based on the moving distance and the moving direction. And then a second X-ray image including the detected part (ROI) of the subject is taken by the image capturing device. The ROI is located at the center of the field of view, such as the second X-ray image. In this way, the positioning system can be moved to the target position more quickly and accurately due to accurate calculation, which reduces the time of positioning and thus reduces exposure dose of the subject and an operator.

Figure 7:
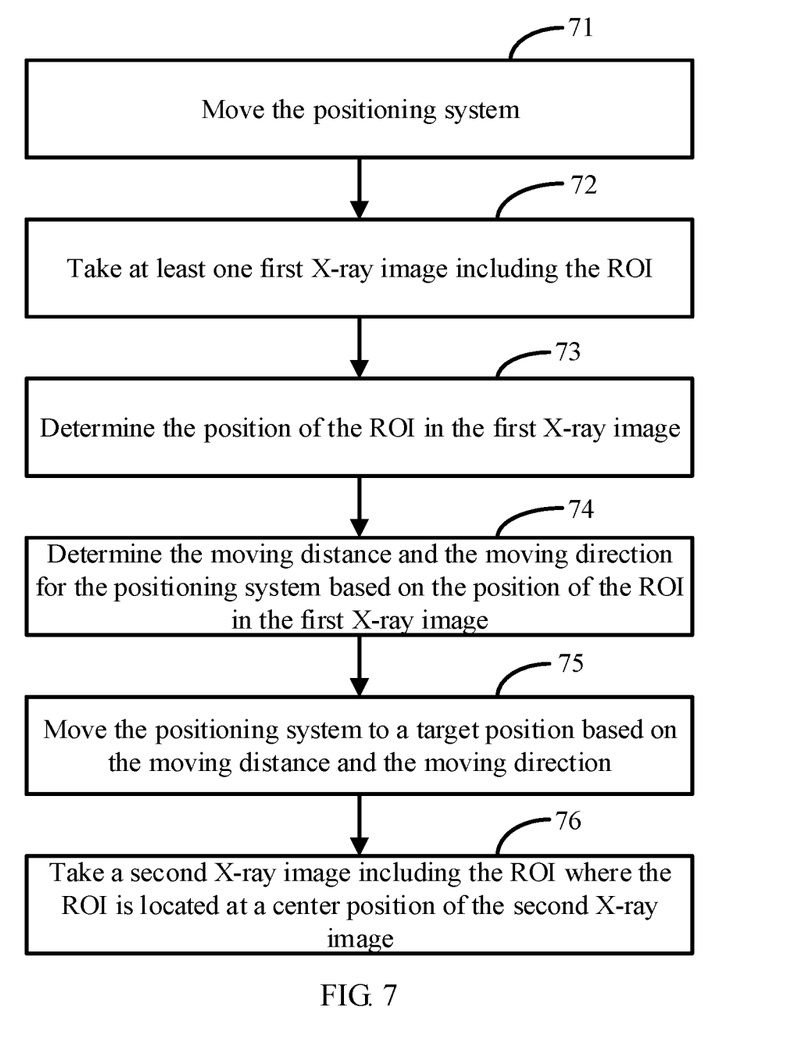
FIG. 7 is a flowchart illustrating an imaging method according to another example of the present disclosure.

FIG. 7 is a flowchart illustrating an imaging method according to another example of the present disclosure. The imaging method may include blocks 71-76.

At block 71, the positioning system is moved.

When the detected part of the subject is outside the X-ray radiation range, the positioning system may be moved in such a way that the detected part of the subject is wholly or partially within the X-ray radiation range or close to the X-ray radiation range, which can be referred to as "pre-placing". Ideally, after the positioning system is moved, the detected part of the subject can be wholly within the X-ray radiation range, so that the first X-ray image taken may contain a complete ROI. However, in actual practice, position error caused by pre-placing the positioning system of one time may be relatively large, for example, position error caused by manually moving the positioning system is relatively large and may result in that the detected part of the subject is wholly or partially outside the X-ray radiation range so that the X-ray image taken does not contain the ROI or contain part of the ROI. Thus, the positioning system may be moved again to adjust the position of the positioning system until the X-ray image taken contains the complete ROI.

In an example of the present disclosure, it is selected to move the positioning system manually. For example, in one case, the bed is moved by operating a rocker or a button nearby the bed; in the other case, the bed and/or the gantry is moved to a preset position by selecting the preset position. Different preset positions may be set based on different examinations, for example, a preset position for heart examination and a preset position for nerve examination. The positioning system is moved such that the first X-ray image to be taken contains the ROI.

At block 72, at least one first X-ray image including the ROI is taken.

At block 73, the position of the ROI in the first X-ray image is determined.

At block 74, the moving distance and the moving direction for the positioning system are determined based on the position of the ROI in the first X-ray image.

At block 75, the positioning system is moved to a target position based on the moving distance and the moving direction.

At block 76, a second X-ray image including the ROI is taken where the ROI is located at a center position of the second X-ray image.

Blocks 72-76 in the example of the present disclosure are similar to blocks 11-15 in the example shown in FIG. 1 and further detail is omitted for brevity. Please see the above examples shown in FIG. 1 for more detail.

According to an example of the present disclosure, the positioning system may be pre-placed before the first X-ray image is taken, so that the first X-ray image to be taken contains the ROI, to subsequently facilitate controlling the positioning system to move to the target position based on the position of the ROI in the first X-ray image taken. Further, during the pre-placing, there is no X-ray scan, thereby lowering exposure dose of the subject and an operator.

Corresponding to the above examples of the imaging method, the present disclosure also provides an example of an imaging system.

Figure 8:
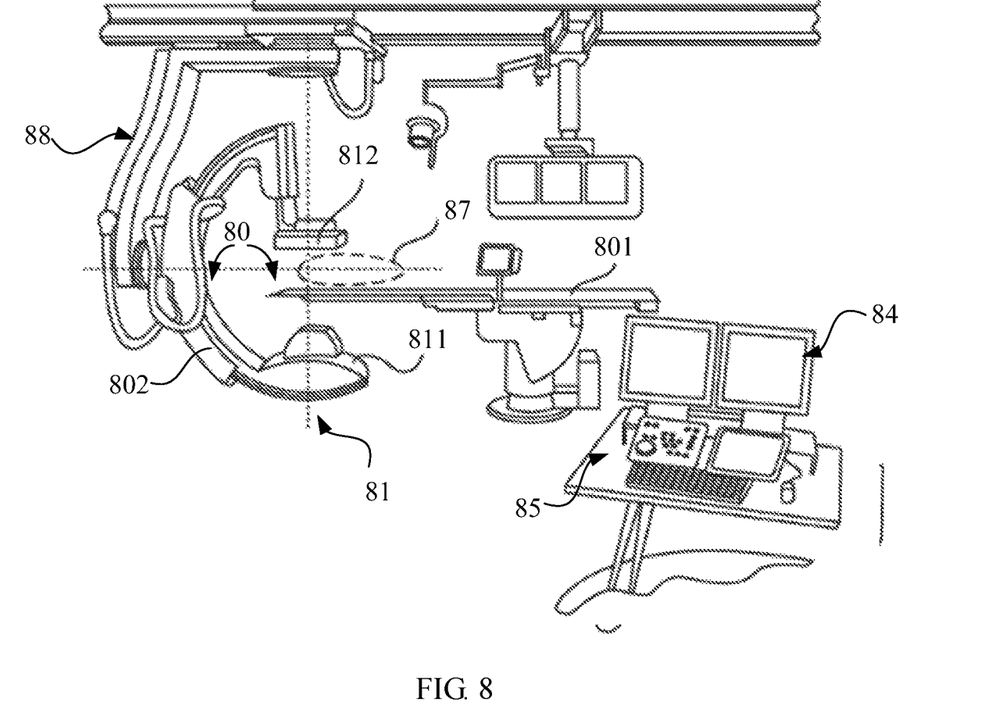
FIG. 8 is a schematic diagram illustrating a hardware structure of an imaging system according to an example of the present disclosure.

The above imaging method may be applied to an imaging system. FIG. 8 is a schematic diagram illustrating a hardware structure of an imaging system according to an example of the present disclosure. The imaging system may be used to realize blood vessel subtraction, for example subtractions of blood vessels in heart or other parts of the subject. Further, the imaging system may be used to reconstruct a three-dimensional image of blood vessels and/or realize tracking angiography of lower limb artery. The imaging system may include an image capturing device 81, a positioning system 80, an image displaying device 84 and a computer 85.

The image capturing device 81 may include a transmitter 811 and a receiver 812. The transmitter 811 may be used to send X-rays to a subject 87 where the subject 87 lies on a bed 801. The receiver 812 and the transmitter 811 are arranged oppositely for detecting X-rays passing through the subject 87. In an example, the receiver 812 may include an image enhancer system and a video camera. The image enhancer system may be configured to convert invisible X-rays into a visible light beam corresponding to the invisible X-rays. The video camera may be configured to take the visible light beam and convert it into video signals. In other examples, the receiver 812 includes a solid state flat panel detector or another type of X-ray detector.

The positioning system 80 may include the bed 801, or include a gantry 802 or include both of the bed 801 and the gantry 802. The transmitter 811 and the receiver 812 are respectively mounted on opposite ends of the gantry 802. The receiver is opposite to the transmitter. When an X-ray image is taken, the transmitter 811 and the receiver 812 are fixed to opposite sides of the subject 87 through the gantry 802. The bed 801 may be driven by a bed driver (not shown) to move. The bed driver may be controlled by a controller (not shown) nearby the bed 801 to move the bed 801. In addition, the bed driver may be integrated into the bed 801. The controller nearby the bed 801 may include a control panel, a rocker and/or a button, and so on.

In an illustrated example, the gantry 802 is a C-shaped arm. In other examples, the gantry 802 is a G-shaped arm or of another shape. The gantry 802 may be rotatably mounted on a fixing support 88 and may slide relative to the support 88 along a preset track. Thus, a position and an angle of the transmitter 811 and the receiver 812 relative to the subject 87 may be adjusted according to actual applications. The gantry 802 may be driven by a gantry driver (not shown) to move.

The computer 85 may be used to process signals obtained by the image capturing device 81 to generate control signals for controlling the positioning system 80 to move as well as an X-ray image. The computer 85 may include a processor and a storage medium. The storage medium is used to store data such as readable instructions and the processor is used to read the data such as the readable instructions stored on the storage medium and execute operations indicated by the readable instructions.

The image displaying device 84 may include one or more displays for displaying images and/or parameters, and so on. The displays may be placed in positions that are convenient for an operator to observe, such as in a control room, in an operating room and nearby the bed.

Figure 9:
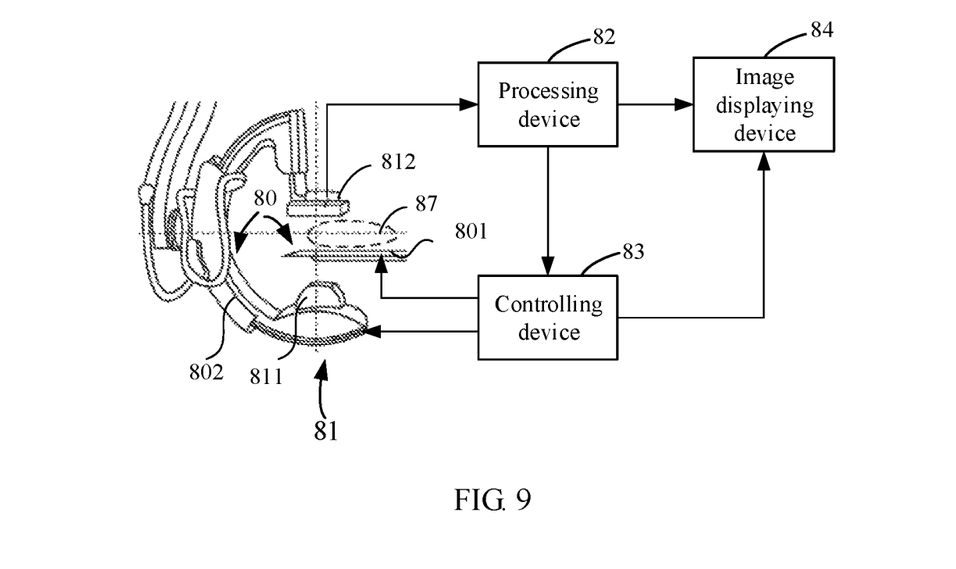
FIG. 9 is a schematic diagram illustrating a functional devices of an imaging system according to an example of the present disclosure.

FIG. 9 is a schematic diagram illustrating a functional device of an imaging system according to an example of the present disclosure. The imaging system may include an image capturing device 81, a positioning system 80, a processing device 82 and a controlling device 83. The image capturing device 81 is configured to take a first X-ray image including a region of interest (ROI) of a subject; the positioning system 80 is capable of being moved to adjust a position of the ROI in the first X-ray image; the processing device 82 is configured to determine a moving distance and a moving direction for a positioning system based on the position of the ROI in the first X-ray image, where the functions of the processing device 82 can be implemented by the processor in the computer 85; the controlling device 83 is configured to control the positioning system to move to a target position based on the moving distance and the moving direction for the positioning system; and then the image capturing device 81 is configured to take a second X-ray image including the ROI, where the ROI is located at a center position of the second X-ray image.

In an example, the processing device 82 is configured to determine a distance and a positional direction between the center point of the first X-ray image and the center point of the ROI in the first X-ray image as a center point positional relationship; determine the moving distance for the positioning system based on the distance in the center point positional relationship; and determine the moving direction for the positioning system based on the positional direction in the center point positional relationship.

In an example, the positioning system 80 may include a bed 801 and a gantry 802. The processing device 82 is configured to obtain a position of the bed 801 and a position of the gantry 802 when the first X-ray image is taken; and determine the moving distance for the positioning system based on the position of the bed, the position of the gantry and the distance in the center point positional relationship. In an example, the processing device 82 is further configured to determine a first relationship between the distance in the center point positional relationship and the moving distance for the positioning system 80 based on the position of the bed 801 and the position of the gantry 802, and determine the moving distance for the positioning system 80 based on the distance in the center point positional relationship and the first relationship. The controlling device 83 is configured to move at least one of the bed and the gantry based on the moving distance for the positioning system 80. In an example, the position of the bed 801 is recorded and fed back to the processing device 82 by a bed position recording and feedback device (not shown), and the position of the gantry 802 is recorded and fed back to the processing device 82 by a gantry position recording and feedback device (not shown). In other examples, the position of the positioning system 80 may also be measured and fed back with other devices.

In an example, the processing device 82 is configured to determine a unit moving distance corresponding to a unit pixel size in the first X-ray image; represent the distance in the center point positional relationship by a pixel distance; and determine the moving distance for at least one of the bed and the gantry based on the pixel distance and the unit moving distance.

In an example, the gantry 802 is respectively provided with the transmitter 811 and the receiver 812 which is opposite to the transmitter and includes receiving units. The processing device 82 is configured to determine a first distance between the transmitter 811 and the bed 801, a second distance between the transmitter 811 and the receiver 812 and a size of each of the receiving units in the receiver 812; and determine the moving distance for the positioning system based on the first distance, the second distance, the size of each of the receiving units and the distance in the center point positional relationship.

In an example, the processing device 82 is configured to determine a coordinate of the center point of the first X-ray image; determine a mean value of abscissas of all pixel points in the ROI and a mean value of ordinates of all pixel points in the ROI as a coordinate of the center point of the ROI; and determine the distance and the positional direction between the center point of the first X-ray image and the center point of the ROI in the first X-ray image based on the coordinate of the center point of the first X-ray image and the coordinate of the center point of the ROI.

The imaging system shown in FIG. 9 may be used to execute the above imaging method. The image capturing device 81 may be used to execute block 11 and block 15, the processing device 82 may be used to execute blocks 12-13 and the controlling device 83 may be used to execute block 14.

The processing device 82 may be implemented by software, hardware and/or a combination thereof and may be integrated into the computer 85. The controlling device 83 may be implemented by software, hardware and/or a combination thereof and may be integrated into the computer 85 and may also be integrated into a controller nearby the bed.

The controlling device 83 may be used to control a bed driver and a gantry driver to drive the bed 801 and/or the gantry 802 to move.

In an example, the processing device 82 is configured to calculate the moving distance for the positioning system when the ROI in the first X-ray image is moved to the center point of the first X-ray image based on the first X-ray image including the ROI pre-taken by the image capturing device 81, and trigger the controlling device 83 to control the positioning system to move to a target position so that the detected part of the subject is located at the center of the field of view and the ROI is located at the center of the X-ray image. In this way, the positioning system 80 can be moved to the target position more quickly and accurately due to accurate calculation so as to reduce the time of positioning, thereby lowering exposure dose of the subject 87 and an operator.

Details of the implementation process of the functions and effects of different devices in the above-described system may be seen from the implementation process of corresponding blocks in the above-described method, which will not be redundantly described herein.

Since the system examples substantially correspond to the method examples, a reference may be made to part of the descriptions of the method examples for the related part. The system examples described above are merely illustrative, where the devices described as separate members may be or not be physically separated, and the members displayed as devices may be or not be physical devices, i.e., may be located in one place, or may be distributed to a network devices.

The foregoing disclosure is merely illustrative of examples of the present disclosure but not intended to limit the present disclosure, and any modifications, equivalent substitutions, adaptations thereof made within the spirit and principles of the disclosure shall be encompassed in the scope of protection of the present disclosure.

What is claimed is:

1. An imaging method, comprising:
    generating a first X-ray image including a region of interest (ROI) of a subject by an image capturing device, the image capturing device comprising a transmitter configured to emit X-rays to the subject and a receiver configured to detect X-rays passing through the subject, the ROI of the subject indicating a detected part of the subject;
    determining a distance and a positional direction between a center point of the first X-ray image and a center point of the ROI in the first X-ray image as a center point positional relationship;
    determining a moving distance and a moving direction for a positioning system based on the center point positional relationship, wherein the positioning system is configured to be moved to adjust a positional relationship between the image capturing device and the subject;
    moving the positioning system based on the moving distance and the moving direction; and
    taking a second X-ray image including the ROI by the image capturing device, wherein the ROI is located in a center position of the second X-ray image.

2. The method according to claim 1, wherein determining the moving distance and the moving direction for the positioning system based on the center point positional relationship comprises:

determining the moving distance for the positioning system based on the distance in the center point positional relationship; and
determining the moving direction for the positioning system based on the positional direction in the center point positional relationship.

3. The method according to claim 2, wherein the determining of the moving distance for the positioning system based on the distance in the center point positional relationship comprises:
obtaining a position of a bed involved in the positioning system and a position of a gantry involved in the positioning system when the subject lies on the bed and the image capturing device provided on the gantry takes the first X-ray image; and
determining the moving distance for the positioning system based on the position of the bed, the position of the gantry and the distance in the center point positional relationship.

4. The method according to claim 3, wherein determining the moving distance for the positioning system based on the position of the bed, the position of the gantry and the distance in the center point positional relationship comprises:
determining a device moving distance corresponding to a unit pixel size in the first X-ray image;
representing the distance in the center point positional relationship by a pixel distance; and
determining a moving distance for at least one of the bed and the gantry based on the pixel distance and the device moving distance.

5. The method according to claim 4, wherein
the gantry respectively comprises:
the transmitter; and
the receiver which is opposite to the transmitter and includes a plurality of receiving devices; and wherein
determining the device moving distance corresponding to the unit pixel size in the first X-ray image, comprising:
determining a first distance between the transmitter and the bed;
determining a second distance between the transmitter and the receiver;
determining a size of each of the plurality of receiving devices in the receiver; and
determining the device moving distance corresponding to the unit pixel size based on the first distance, the second distance and the size of each of the plurality of receiving devices.

6. The method according to claim 1, wherein the determining of the distance and the positional direction between the center point of the first X-ray image and the center point of the ROI in the first X-ray image comprises:
determining a coordinate of the center point of the first X-ray image;
determining a mean value of abscissas of all pixel points in the ROI and a mean value of ordinates of all pixel points in the ROI as a coordinate of the center point of the ROI; and
determining the distance and the positional direction between the center point of the first X-ray image and the center point of the ROI in the first X-ray image based on the coordinate of the center point of the first X-ray image and the coordinate of the center point of the ROI.

7. The method according to claim 1, further comprising:
moving the positioning system such that the first X-ray image to be taken contains the ROI.

8. An imaging system, comprising:
an image capturing device, configured to generate a first X-ray image including a ROI of a subject and a second X-ray image including the ROI, wherein the ROI is located at a center position of the second X-ray image, the image capturing device comprising a transmitter configured to emit X-rays to the subject and a receiver configured to detect X-rays passing through the subject, the ROI of the subject indicating a detected part of the subject;
a positioning system configured to be moved to adjust a position of the ROI in the first X-ray image;
a processing device, configured to:
determine a distance and a positional direction between a center point of the first X-ray image and a center point of the ROI in the first X-ray image as a center point positional relationship, and
determine a moving distance and a moving direction for a positioning system based on the center point positional relationship; and
a controlling device, configured to move the positioning system based on the moving distance and the moving direction.

9. The system according to claim 8, wherein the processing device is further configured to:
determine the moving distance for the positioning system based on the distance in the center point positional relationship; and
determine the moving direction for the positioning system based on the positional direction in the center point positional relationship.

10. The system according to claim 9, wherein the processing device is further configured to:
obtain a position of a bed involved in the positioning system and a position of a gantry involved in the positioning system when the subject lies on the bed and the image capturing device provided on the gantry takes the first X-ray image; and
determine the moving distance for the positioning system based on the position of the bed, the position of the gantry and the distance in the center point positional relationship.

11. The system according to claim 10, wherein the controlling device is further configured to move at least one of the bed and the gantry based on the moving distance for the positioning system.

12. The system according to claim 10, wherein the processing device is further configured to:
determine a device moving distance corresponding to a unit pixel size in the first X-ray image;
represent the distance in the center point positional relationship by a pixel distance; and
determine a moving distance for at least one of the bed and the gantry based on the pixel distance and the device moving distance.

13. The system according to claim 12, wherein
the gantry respectively comprises:
the transmitter; and
the receiver which is opposite to the transmitter and includes a plurality of receiving devices;
determining the device moving distance corresponding to the unit pixel size in the first X-ray image comprising:
determining a first distance between the transmitter and the bed;

determining a second distance between the transmitter and the receiver;

determining a size of each of the plurality of receiving devices in the receiver; and determining the device moving distance corresponding to the unit pixel size based on the first distance, the second distance and the size of each of the plurality of receiving devices.

14. The system according to claim 9, wherein the processing device is further configured to:

determine a coordinate of the center point of the first X-ray image;

determine a mean value of abscissas of all pixel points in the ROI and a mean value of ordinates of all pixel points in the ROI as a coordinate of the center point of the ROI; and determine the distance and the positional direction between the center point of the first X-ray image and the center point of the ROI in the first X-ray image based on the coordinate of the center point of the first X-ray image and the coordinate of the center point of the ROI.

\* \* \* \* \*